United States Patent [19]

Breliere et al.

[11] Patent Number: 4,746,654

[45] Date of Patent: May 24, 1988

[54] ANTI-INFLAMMATORY PRODUCTS DERIVED FROM METHYLENE-DIPHOSPHONIC ACID, AND PROCESS FOR THEIR PREPARATION

[75] Inventors: Jean C. Breliere; Xavier Emonds-Alt, both of Montpellier; Georges Garcia, Saint-Gely-du-Fesc, all of France

[73] Assignee: Sanofi, Paris, France

[21] Appl. No.: 858,573

[22] Filed: Apr. 24, 1986

Related U.S. Application Data

[63] Continuation of Ser. No. 518,427, Jul. 29, 1983.

[30] Foreign Application Priority Data

Jul. 29, 1982 [FR] France ................... 82 13250

[51] Int. Cl.$^4$ ............... A61K 31/66; C07F 9/38
[52] U.S. Cl. ................. 514/108; 260/501.21; 514/824; 514/877; 558/155
[58] Field of Search .............. 260/501.21, 932; 514/108, 824, 103, 877, 127, 712; 558/155

[56] References Cited

U.S. PATENT DOCUMENTS

| | | | |
|---|---|---|---|
| 3,299,123 | 1/1967 | Fitch et al. | 260/501.21 |
| 3,654,151 | 4/1972 | King et al. | 260/501.21 |
| 3,683,080 | 8/1972 | Francis | 424/204 |
| 3,705,191 | 12/1972 | Kerst | 260/501.21 |
| 3,957,858 | 5/1976 | Kerst | 260/501.21 |
| 4,071,584 | 1/1978 | Birum | 260/932 |
| 4,171,373 | 10/1979 | Diamond | 514/712 |
| 4,264,582 | 4/1981 | Flora et al. | 514/108 |

FOREIGN PATENT DOCUMENTS 0015370  9/1980  European Pat. Off. .

OTHER PUBLICATIONS

Chemical Abstracts, vol. 93, No. 25, 22 Dec. 1980, p. 877, 239648z (Columbus, Ohio, US) & JP-A-80 98 193 (Nissan Chemical Industries Ltd.), 25 Jul. 1980.
Synthesis, No. 2, Feb. 1980, Georg Thieme Verlag, Stuttgart, N.Y., M. Mikolajczyk et al, "Sulphenylation of Phosphonates. A Facile Synthesis of Alpha-Phosphoryl Sulphides and S,S-Acetals of Oxomethanephosphonates", pp. 127-129.

Primary Examiner—Glennon H. Hollrah
Assistant Examiner—Raymond Covington
Attorney, Agent, or Firm—Stevens, Davis, Miller & Mosher

[57] ABSTRACT

The present invention relates to products of the formula

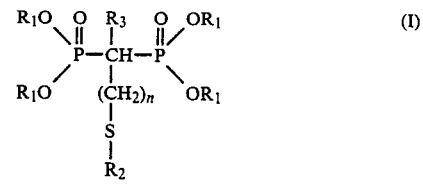

where $R_1$ is H or alkyl, n is an integer from 0 to 10, and $R_2$ is chosen from amongst H, unsubstituted or substituted alkyl radicals, a

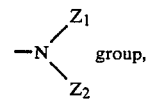

a substituted or unsubstituted phenyl radical, a

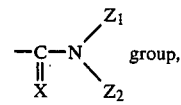

where X is oxygen or sulfur, or a heterocyclic radical with 5 or 6 members, which may or may not be fused to a benzene ring and $R_3$ is H or OH.

The present invention also relates to a process for the preparation of the products of the formula (I), and to the drugs, having in particular an anti-inflammatory effect, containing a product of the formula (I).

2 Claims, No Drawings

ANTI-INFLAMMATORY PRODUCTS DERIVED FROM METHYLENE-DIPHOSPHONIC ACID, AND PROCESS FOR THEIR PREPARATION

This application is a continuation of application Ser. No. 518,427, filed July 29, 1983.

The present invention relates to novel derivatives of methylene-diphosphonic acid, possessing therapeutic properties permitting their use in the treatment of inflammation symptoms.

More precisely, the compounds according to the invention correspond to the general formula:

$$\begin{array}{c} R_1O\phantom{xx}O\phantom{xx}R_3\phantom{xx}O\phantom{xx}OR_1 \\ \diagdown\|\phantom{x}|\phantom{x}\|\diagup \\ P-C-P \\ \diagup\phantom{xx}|\phantom{xx}\diagdown \\ R_1O\phantom{xxx}(CH_2)_n\phantom{xx}OR_1 \\ | \\ S \\ | \\ R_2 \end{array} \quad (I)$$

where:

$R_1$ is hydrogen or a straight or branched lower alkyl group having from 1 to 4 carbon atoms, $R_2$ is:

hydrogen, an alkyl group which is unsubstituted or substituted by a hydroxyl group, a thiol group, one or more halogen atoms, an alkoxycarbonyl group or a $$-N\diagup^{Z_1}_{\diagdown Z_2} \text{ group,}$$

where $Z_1$ and $Z_2$, considered independently of one another, are hydrogen or a lower alkyl group, a phenyl group which is unsubstituted or has one or more halogen, nitro group, lower alkyl group, lower alkoxy group, trifluoromethyl, $NH_2$ group, COOH group or COOalkyl group, a $$\begin{array}{c} X\phantom{xx}Z_1 \\ \|\phantom{x}\diagup \\ -C-N \\ \phantom{xxx}\diagdown \\ \phantom{xxxx}Z_2 \end{array} \text{ group,}$$

where X is oxygen or sulfur and $Z_1$ and $Z_2$ are as defined above, a heterocyclic radical with 5 or 6 members, containing 1 or 2 heteroatoms chosen from amongst nitrogen and sulfur, or, a heterocyclic radical with 5 members fused to a benzene ring and having the formula $$\begin{array}{c} X\phantom{xxxx}R_4 \\ \diagup\phantom{x}\diagdown \\ \phantom{x}|\phantom{xx}| \\ \phantom{x}N \end{array}$$

where X is oxygen, an NH group or sulfur and $R_4$ is hydrogen or a halogen atom, preferably chlorine, $R_3$ is hydrogen or a hydroxyl group, and n is an integer between 0 and 10, with the proviso that n cannot be 0 if $R_3$ is OH.

If $R_1$ is hydrogen, the acids of the formula (I) are capable of forming salts with inorganic or organic bases. These salts form an integral part of the invention.

Some of the compounds of the formula (I) have already been described but in not case have their therapeutic properties been mentioned.

Thus, U.S. Pat. No. 4,071,584 describes, but does not claim, compounds of the formula (I), where $R_1$ is $CH_3$ or $C_2H_5$, $R_3$ is H and $R_2$ is the $$\begin{array}{c} \phantom{xxxx}OP \\ \phantom{xx}\diagup \\ \phantom{x}|\phantom{xx}| \\ \phantom{x}\diagdown \\ Q \end{array} \text{ group,}$$

where P is $CH_3$ and Q is Br or $NO_2$, or P is H and Q is Br, $NO_2$ or Cl, and n is 0.

This patent also describes the acid (I) where $R_1$ is H, P is H and Q is Cl. These products are obtained by transformation of phosphorus-containing derivatives which are themselves claimed as corrosion inhibitors, oil additives or flame retardants.

In the review publication Synthesis, of February 1980, pages 127–129, the authors describe, inter alia, the compound (I), where $R_1$ is $C_2H_5$, $R_3$ is H, $R_2$ is $C_6H_5$ and n is 0, without mentioning any therapeutic property of this compound.

Japanese patent application No. 80.193 [Chemical Abstracts 93, 23648z, (1980)] cites, as herbicides, the compounds (I) where $R_1$ is H, $R_2$ is pyridyl, $R_3$ is H and n is 0.

Zeitschrift fur Praktische Chemie, (1970 (3), 475–482, describes the compound (I), where $R_1$ is H, $R_2$ is $CH_3$, $R_3$ is H and n is 0. The article concerned is purely chemical.

The other compounds (I) are novel.

The present invention also relates to a process for the preparation of the compounds of the formula (I). If $R_3$ is H, the following process is employed:

$$\begin{array}{c} R_1'O\phantom{x}O\phantom{xxxx}O\phantom{x}OR_1' \\ \diagdown\|\phantom{xxxx}\|\diagup \\ P-CH_2-P \\ \diagup\phantom{xxxxxx}\diagdown \\ R_1'O\phantom{xxxxxx}OR_1' \\ 1 \end{array} \longrightarrow \begin{array}{c} R_1'O\phantom{x}O\phantom{x}M\phantom{x}O\phantom{x}OR_1' \\ \diagdown\|\phantom{x}|\phantom{x}\|\diagup \\ P-CH-P \\ \diagup\phantom{xxxxxx}\diagdown \\ R_1'O\phantom{xxxxxx}OR_1' \end{array} \longrightarrow$$

$$\begin{array}{c} R_1'O\phantom{xx}O\phantom{xxxxx}O\phantom{xx}OR_1' \\ \diagdown\|\phantom{xxxxxx}\|\diagup \\ P\phantom{xx}-CH-P \\ \diagup\phantom{xxxx}|\phantom{xxxx}\diagdown \\ R_1'O\phantom{xx}(CH_2)_n\phantom{xx}OR_1' \\ | \\ S \\ | \\ R_2 \end{array} \quad (I)$$

$R_1'$ = lower alkyl
M = Na or K
$R_1$ = lower alkyl

The starting material used is a lower alkyl ester of methylene-diphosphonic acid 1, of which the corresponding sodium derivative is prepared by reaction with a sodium-introducing agent such as sodium hydride, in a suitable solvent such as a benzene hydrocarbon, preferably toluene, or in dimethylformamide.

The reaction is carried out at a temperature of between 0° and 50° C. and preferably at ambient temperature (20° C.). It is also possible to prepare the metal derivative by reaction with potassium hydroxide in toluene.

In the metal derivative thus obtained, which is not isolated, the metal atom is then replaced by the —(CH$_2$)$_n$—S—R$_2$ group.

If n is 0, the sodium derivative is reacted with the disulfide R$_2$S—S—R$_2$ in the solvent used to prepare the sodium derivative. The reaction temperature and time vary considerably depending on the reagents used. The reaction temperature is between 20° C. and the boiling point of the solvent, whilst the reaction time varies from a few hours to several days.

The disulfide can also be replaced by the corresponding sulfenyl chloride R2SCl.

If n is other than 0, the sodium derivative is reacted with a halogen compound Hal(CH$_2$)$_n$—S—R$_2$ at a temperature between ambient temperature and the reflux temperature of the solvent. A variant of this process consists of using a dihalogen derivative Hal—(CH$_2$)$_n$—Hal and then reacting the intermediate thus obtained with the thiol R$_2$SH.

Finally, if n is 3, a variant of the process consists of carrying out a substitution reaction between the diphosphonic ester, as indicated and an allyl halide, and thereafter reacting the allyl-diphosphonate thus obtained with the thiol R$_2$SH. If the thiol R$_2$SH used is volatile, it may be necessary to carry out the reaction in an autoclave at a temperature of between 80° and 150° C.

In every case, if the —(CH$_2$)$_n$—S—R$_2$ group introduced contains reactive substituents, they have to be blocked beforehand by means of a reagent which can subsequently easily be removed.

Thus, for example, OH groups can be blocked by forming a dihydropyran ester and carboxyl groups can be blocked in the form of the sodium salt.

If R$_3$ is OH, the compounds (I) are prepared in accordance with the following reaction scheme:

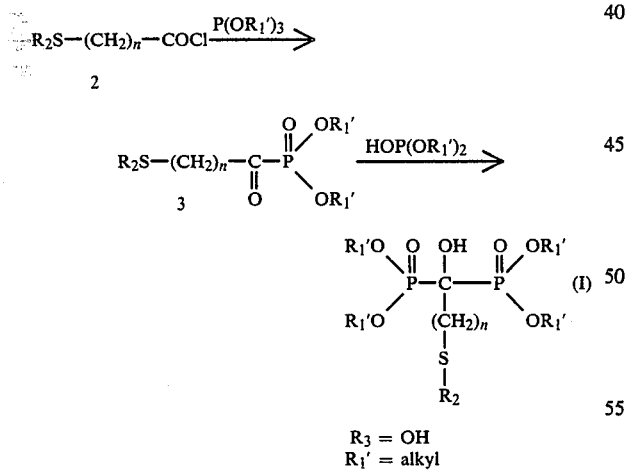

The acid chloride 2 is reacted with a trialkyl phosphite at a temperature between 20° and 50° C. The compound 3 is thus obtained. This is not isolated, but treated with a dialkyl phosphite in the presence of a secondary amine such as dibutylamine at a temperature of between 0° and 20° C.

In a variant of this process, the compound 2 is replaced by a chloride of a halogen-containing acid Hal—(CH$_2$)$_n$—COCl (4), which similarly leads, in two stages, to the compound:

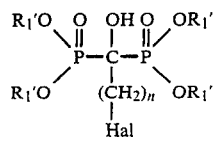

This compound, when treated with a thiol R$_2$SH in a solvent such as acetonitrile in the presence of 1,5-diazabicyclo-(5,4,0)-undec-5-ene at a low temperature leads to the compounds (I), where R$_3$ is OH and R$_1$ is alkyl.

From compounds (I) where R$_1$ is alkyl, the compounds (I) where R$_1$ is hydrogen are obtained by hydrolysis. This is carried out by heating the ester in dilute hydrochloric acid under reflux for a period which varies from a few hours to 24 hours, depending on the particular case. After isolation by evaporation, the acid thus obtained can be converted in a known manner into one of its salts. This process is carried out in a hot solvent so that the salt crystallizes on cooling.

The hydrolysis of the esters can also be carried out by treatment with trimethylsilyl bromide in a solvent such as carbon tetrachloride at a not very high temperature, most commonly at ambient temperature.

The examples which follow are given by way of illustration of the invention and do not imply any limitation.

EXAMPLE 1

Tetramethyl benzoxazol-2-yl-thiomethylene-diphosphonate (SR 41625)

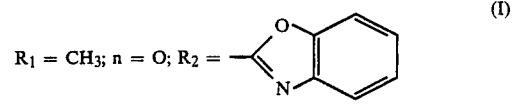

2.5 g of sodium hydride are added to a mixture of 24 g of tetramethyl methylene-diphosphonate and 50 ml of dimethylformamide under a nitrogen atmosphere, at 50° C. The mixture is stirred for 1 hour at 15° C. and 44 g of dibenzoxazol-2-yl-disulfide are then added at 20° C. Stirring at 25° C. is continued for 68 hours and the dimethylformamide is then evaporated in vacuo at 20° C. The residue, dissolved in methylene chloride, is chromatographed on a column of 500 g of silica.

On eluting with methylene chloride, the unreacted starting materials are removed, and on subsequent eluting with a 96:4 (volume/volume) mixture of methylene chloride/ethanol, the expected product is obtained in a form which is still impure.

It is purified by renewed chromatography, on 160 g of silica. Using a 97:3 (volume/volume) methylene chloride/ethanol solvent mixture, a product is obtained which crystallizes on cooling the solution to 0° C.; melting point: 76°-8° C.

On proceeding in the same manner with the tetraisopropyl ester of methylene-diphosphonic acid and varying the disulfide used, the various esters shown in Table 1 are obtained.

TABLE 1

| Code No. | n | R$_2$ | Working conditions (temperature and heating time) | Physical properties |
|---|---|---|---|---|
| SR 41265 | 0 | 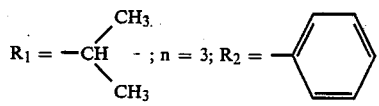 Cl | 90° C. - 5 hours | 140° C. (acetonitrile) |
| SR 41452 | 0 | 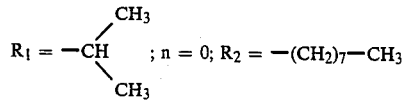 COOH | 25° C. - 6 hours | Yellow oil Chromatography on a thin layer of silica, ethyl acetate/ethanol, 8:2 (volume/volume); Rf = 0.7 |

EXAMPLE 2

Tetraisopropyl 4-phenylthio-butylene-1,1-diphosphonate (SR 41341)

$R_1 = -CH \begin{smallmatrix} CH_3 \\ CH_3 \end{smallmatrix}$ ; n = 3; $R_2 = $   (I)

The sodium derivative of tetraisopropyl methylenediphosphonate (34.4 g) is prepared as in Example 1, and thereafter 28.7 g of 1-bromo-3-phenylthio-propane are added and the mixture is heated at 100° C. for 1 hour.

The solvent is evaporated to dryness in vacuo and the residue is then taken up in 500 ml of water and extracted with methylene chloride. The organic phase is separated off and dried over sodium sulfate, and the solvent is evaporated in vacuo. The residue is heated at 130° C. in a high vacuum to remove the volatile products and is then chromatographed on a column of silica gel, elution being carried out with a 99:1 (volume/volume) mixture of chloroform/methanol.

An oil (23 g) is thus obtained, which is again purified by chromatography on silica gel, using the same solvent system. Chromatography on a thin layer of silica, using a 95:5 (volume/volume) butan-2-one/water mixture as the solvent system gives a spot of Rf 0.57.

EXAMPLE 3

Tetraisopropyl n-octylthiomethylene-diphosphonate (SR 41454)

$R_1 = -CH \begin{smallmatrix} CH_3 \\ CH_3 \end{smallmatrix}$ ; n = 0; $R_2 = -(CH_2)_7-CH_3$  (I)

The method of Example 1 is followed, using a mixture of anhydrous toluene and dimethylformamide as the solvent.

After heating for 16 hours at 100° C., the same treatment yields the expected product in the form of an oil, characterized by an Rf of 0.65 in chromatogrphy on a thin layer of silica using an 8:2 (volume/volume) ethyl acetate/ethanol mixture as the solvent system.

On following the same procedure but replacing the dioctyl-disulfide by an equivalent amount of di-p-tolyl-disulfide, tetraisopropyl p-tolythiomethylene-diphosphonate (SR41455) is obtained as an oil, characterised by an Rf of 0.57 in chromatography on a thin layer of silica using an 8:2 (volume/volume) ethyl acetate/ethanol mixture as the solvent system.

Similarly, using di-(3-trifluoromethyl-phenyl) disulfide, tetraisopropyl (3-trifluoromethyl-phenylthio)-methylenediphosphonate is obtained; Rf: 0.51 (95:5 (volume/volume) ethyl acetate/ethanol) (SR 42248).

Finally, using di-(3-trifluoromethyl-4-nitro-phenyl) disulfide, the same method gives tetraisopropyl (3-trifluoromethyl-4-nitrophenylthio)-methylene-diphosphonate; Rf: 0.51 (95:5 (volume/volume) ethyl acetate/ethanol) (SR 42247).

EXAMPLE 4 tetraisopropyl 7-(4-nitrophenylthio)-heptylidene-1,1 diphosphonate (SR 42147)

$R_1 = -CH \begin{smallmatrix} CH_3 \\ CH_3 \end{smallmatrix}$ ; n = 6; $R_3 = H$; $R_2 = $ 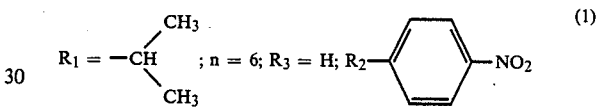 —NO$_2$  (1)

3.8 g of a 50% strength suspension of sodium hydride in oil is added, a little at a time, to a solution of 27 g of tetraisopropyl methylene-diphosphonate in 200 ml of toluene. After all has been added, the mixture is stirred for 1 hour, 27 g of 1-(4-nitrophenylthio)-6-bromo-hexane are then added and the whole is heated for 3 hours at 80° C.

The mixture is evaporated to dryness in vacuo and the residue is taken up in hexane. The solution is washed twice with water and then dried over sodium sulfate. The solvent is evaporated to dryness and the residue is chromatographed on a silica column, elution being carried out with a 98:2 (volume/volume) mixture of methylene chloride/methanol.

8.5 g of an oil are thus obtained, characterized by an Rf of 0.37 in chromatography on a thin layer of silica, using a 95:5 (volume/volume) mixture of ethyl acetate/ethanol as the solvent system.

Proceeding in the same manner but varying the bromine derivative used, the following are obtained:

Tetraisopropyl 7-(4-methoxy-phenylthio)-heptylidene-1,1-diphosphonate (SR 42306)
Rf: 0.37 (95:5 (volume/volume) mixture of ethyl acetate/ethanol);

Tetraisopropyl 7-(4-chloro-phenylthio)-heptylidene-1,1-diphosphonate (SR 41964)
Rf: 0.37 (95:5 (volume/volume) mixture of ethyl acetate/ethanol);

Tetraisopropyl 7-(3,4-dichloro-phenylthio)-heptylidene-1,1-diphosphonate (SR 42146)
Rf: 0.37 (95:5 (volume/volume) mixture of ethyl acetate/ethanol);

Tetraisopropyl 7-(4-chloro-phenylthio)-undecylidene-1,1-diphosphonate (SR 42145)
Rf: 0.37 (95:5 (volume/volume) mixture of ethyl acetate/ethanol).

EXAMPLE 5

Tetraisopropyl (3-phenyl-propylthio)-methylene-diphosphonate (SR 41907)

A mixture of 29.2 g of tetraisopropyl methylene-diphosphonate, 80 ml of toluene, 11.2 g of potassium hydroxide and 23.2 g of di-(3-phenyl-propyl)-disulfide is stirred for 20 hours at 25° C.

The mixture is washed 5 times with 50 ml of water and the solution is then dried over sodium sulfate and evaporated to dryness in vacuo.

An oil is obtained, which is chromatographed over a column of 500 g of silica. After removal of impurities eluted with methylene chloride, elution with a 95:5 (volume/volume) mixture of methylene chloride/ethanol gives the expected product (11.2 g). When chromatographed on a thin layer of silica, using a 95:5 (volume/volume) mixture of ethyl acetate/ethanol, it has an Rf of 0.5.

On following the same procedure but using di-(2-methoxycarbonyl-ethyl)-disulfide, tetraisopropyl (2-methoxycarbonyl-ethylthio)-methylene-diphosphonate (SR 42250) is obtained; Rf=0.37 (using a 95:5 (volume/volume) mixture of ethyl acetate/ethanol).

EXAMPLE 6

Tetraethyl (N,N-diethylthiocarbamylthio)-methylenediphosphonate (SR 41905)

The procedure of Example 3 is followed starting from tetraethyl methylene-diphosphonate and bis-(diethyl-thiocarbamyl)-disulfide. In the same manner as that described, an oil is obtained which has an Rf of 0.5 when chromatographed on a thin layer of silica (using an 8:2 (volume/volume) mixture of ethyl acetate/ethanol).

EXAMPLE 7

Tetraisopropyl perfluorohexylthio-methylene-disphosphonate (SR 42327)

A mixture of 16 g of tetraisopropyl methylene-diphosphonate and 1.05 g of sodium hydride is stirred at 25° C. under a nitrogen atmosphere. After 1 hour 10 ml of perfluorohexylsulfenyl chloride are added. The temperature rises spontaneously to 80° C. This temperature is maintained for 3 hours and the mixture is then poured into 50 ml of water and extracted with ether. The solvent is evaporated and the residue is taken up in 100 ml of hexane. The solution is washed 5 times with 100 ml of water, then dried and concentrated to dryness in vacuo.

The residue is chromatographed on a silica column. The unreacted materials are removed with methylene chloride and the expected product is then eluted with a 97:3 (volume/volume) mixture of methylene chloride/ethanol.

The product is obtained in the form of an oil. Rf=0.60 (using a 95:5 (volume/volume) mixture of ethyl acetate/ethanol).

EXAMPLE 8

Tri-(tertiary butylamine) salt of methylthiomethylene-diphosphonic acid (SR 41036)

(I) $R_1=H$; $n=0$; $R_2=CH_3$ 0.65 g of sodium hydride is added, at 0° C., to a mixture of 8.8 g of tetraisopropyl methylene-diphosphonate in 25 ml of toluene, and the mixture is then stirred for 1 hour at 15° C. 25 ml of dimethyl-disulfide are added and the mixture is then heated at 60° C. for 24 hours. It is concentrated to dryness in vacuo and the residue is then taken up in 250 ml of isopropyl ether. Insoluble material is filtered off and the filtrate is concentrated to dryness. This product is chromatographed on an alumina column (150 g). Elution is first carried out with isopropyl ether to remove impurities and then with methylene chloride, to give the expected product.

3 g of the ester obtained above, in 12 ml of 6N aqueous hydrochloric acid solution, are heated under reflux for 5 hours. The solution is washed 3 times with 30 ml of pentane and the aqueous phase is then decolorized with active charcoal and concentrated to dryness in vacuo.

The crude acid thus obtained is converted to a salt by adding 2.4 g of tertiary butylamine in 200 ml of boiling absolute ethanol. On cooling, the tri-(tertiary butylamine) salt is obtained in the form of a colorless solid; melting point 212° C.

The acids (I) listed in Table 2 are prepared in a similar manner, but varying the disulfides used.

TABLE 2

$$\begin{array}{c} HO\diagdown\overset{O}{\underset{\|}{P}}\diagup\overset{}{\underset{}{\phantom{x}}}\!\!-CH-\!\!\overset{O}{\underset{\|}{P}}\diagup OH \\ HO\diagup\phantom{xxx}\underset{\underset{\underset{R_2}{|}}{\underset{S}{|}}}{(CH_2)_n}\phantom{xxx}\diagdown OH \end{array}$$

| | | | Operating conditions | | |
|---|---|---|---|---|---|
| Code No. | n | R₂ | Substitution temp. and duration | Hydrolysis Conc. of HCl and duration | Product isolated |
| SR 41100 | 0 | —CH(CH₃)₂ | 110° C. 24 hrs | HCl 6N 5 hrs | Di-(tertiary butylamine) salt M.p.: 252° C. |
| SR 41179 | 0 | (pyridyl) | 20° C. 16 hrs | HCl 6N 24 hrs | Hydrochloride M.p.: >280° C. |

TABLE 2-continued $$\begin{array}{c} HO\diagdown\underset{\underset{HO}{\diagup}}{\overset{O}{\overset{\|}{P}}}-CH-\overset{O}{\overset{\|}{\underset{\diagdown OH}{P}}}\diagup OH \\ | \\ (CH_2)_n \\ | \\ S \\ | \\ R_2 \end{array}$$

| Code No. | n | R₂ | Operating conditions Substitution temp. and duration | Hydrolysis Conc. of HCl and duration | Product isolated |
|---|---|---|---|---|---|
| SR 41264 | 0 | 2-pyrimidinyl | 20° C. 3 hrs | HCl 6N 8 hrs | Hydro-chloride M.p.: >300° C. |
| SR 41266 | 0 | (CH₂)₂NH₂ | 20° C. 2 hrs | HCl 8N 18 hrs | Hydro-chloride M.p.: 285–290° C. |
| SR 41344 | 0 | (CH₂)₂N(CH₃)₂ | 20° C. 20 hrs | HCl 8N 18 hrs | Hydro-chloride M.p.: 176° C. |
| SR 41482 | 0 | phenyl | 110° C. 48 hrs | HCl 6N 6 hrs | Tri-(tertiary butylamine) salt M.p.: 24° C. with ½ H₂O |
| SR 41688 | 0 | 3,5-dichlorophenyl | 20° C. 16 hrs | HCl 6N 16 hrs | Free acid M.p.: >260° C. |
| SR 41689 | 0 | 2-chlorophenyl | 20° C. 16 hrs | HCl 6N 16 hrs | Free acid M.p.: 226° C. |
| SR 41690 | 0 | 3-chlorophenyl | 20° C. | HCl 6N | Di-(tertiary butylamine) salt M.p.: 270° C. |

EXAMPLE 9

Di-(tertiary butylamine) salt of (4-chlorophenyl)thiomethylene-diphosphonic acid (SR 41319)

(I) $R_1 = H; n = 0; R_2 = $ 4-chlorophenyl

The procedure followed is as in Example 4, the solvent being dimethylformamide instead of toluene.

To effect the substitution, heating with a disulfide is carried out at 25° for 6 hours. The ester is isolated as indicated in Example 4 and is then hydrolyzed with 12N HCl for 18 hours.

The acid is obtained in the same manner as described previously and is converted to the di-(tertiary butylamine) salt as indicated in Example 4. Melting point: 253° C. (decomposition).

The compounds (I) according to the invention listed in Table 3 are prepared in a similar manner, but varying the disulfides used.

TABLE 3

$$\begin{array}{c} HO\diagdown\overset{O}{\overset{\|}{P}}-CH-\overset{O}{\overset{\|}{P}}\diagup OH \\ HO\diagup \underset{|}{(CH_2)_n}\diagdown OH \\ \underset{|}{S} \\ R_2 \end{array}$$

| Code No. | n | R$_2$ | Substitution temp. and duration | Hydrolysis Conc. of HCl and duration | Product isolated |
|---|---|---|---|---|---|
| SR 41263 | 0 | 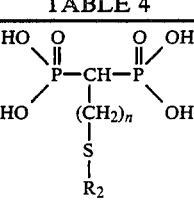 | 20° C. 24 hrs | HCl 6N 12 hrs | Free acid M.p.: >300° C. |
| SR 41388 | 0 | (o-methyl aniline) | 20° C. 4 hrs | HCl 10N 12 hrs | Free acid M.p.: 272° C. (decomposition) (Crystallized with 1 molecule of water) |
| SR 41480 | 0 | (5-chloro-2-formamido-phenyl) | 20° C. 16 hrs | HCl 6N 16 hrs | Free acid M.p.: >260° C. |
| SR 41552 | 0 | CH$_3$—(CH$_2$)$_6$— | 20° C. 18 hrs | HCl 12N 20 hrs | Tertiary butylamine salt M.p.: 218° C. |

EXAMPLE 10

Tertiary butylamine salt of 3-methylthio-propylidene-1,1-diphosphonic acid (SR 41273)

(I) R$_1$=H; n=2; R$_2$=CH$_3$

The procedure followed is as in Example 4, the disulfide being replaced by 1-bromo-2-methylthio-ethane.

After the mixture has been heated for 20 hours at 30° C., the ester is isolated and then hydrolyzed as indicated in Example 4, using 8N HCl at the reflux temperature for 7 hours.

Finally, the acid is converted to a salt by treatment with tertiary butylamine. Melting point: 212°–4° C.

EXAMPLE 11

Di-(tertiary butylamine salt) of 4-phenylthio-butylidene-1,1-diphosphonic acid (SR 41342)

R$_1$ = H; n = 3; R$_2$ = 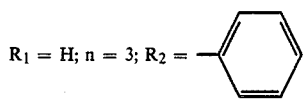   (I)

A solution of 5 g of the ester SR 41341 (Example 1) in 18 ml of 6N hydrochloric acid is heated under reflux for 7 hours. It is evaporated to dryness and the residue is taken up in 25 ml of water. The precipitate is filtered off, dried and recrystallized from acetonitrile, and the product is then converted to a salt with tertiary butylamine. Melting point: 223° C.

Using the same procedure but varying the starting ester, the products listed in Table 4 are obtained.

TABLE 4

$$\begin{array}{c} HO\diagdown\overset{O}{\overset{\|}{P}}-CH-\overset{O}{\overset{\|}{P}}\diagup OH \\ HO\diagup \underset{|}{(CH_2)_n}\diagdown OH \\ \underset{|}{S} \\ R_2 \end{array}$$

| Code No. | n | R$_2$ | Hydrolysis Conc. of HCl and duration | Product isolated |
|---|---|---|---|---|
| SR 41421 | 0 | —(CH$_2$)$_7$CH$_3$ | HCl 12N 16 hrs | Free acid M.p.: 155–160° C. |
| SR 41456 | 0 | 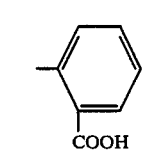 (—C$_6$H$_4$—CH$_3$) | HCl 12 N 16 hrs | Di-(tertiary butylamine) salt M.p.: 255–260° C. (decomposition) |
| SR 41272 | 0 | 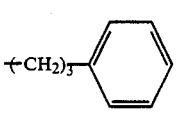 (—C$_6$H$_4$—COOH) | HCl 6N 8 hrs | Tri-(tertiary butylamine) salt M.p.: 198–202° C. |
| SR 41908 | 0 | ⦅CH$_2$⦆$_3$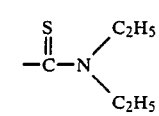 | HCl 12N 16 hrs | Free acid M.p.: 176–8° C. |
| SR 41960 | 0 | $-\overset{\overset{S}{\|}}{C}-N\diagdown^{C_2H_5}_{C_2H_5}$ | HCl 12N 16 hrs | Di-(tertiary butylamine) salt M.p.: 235° C. (decomposition) |

TABLE 4-continued $$\begin{array}{cc} HO\diagdown\underset{\|}{P}{-}CH{-}\underset{\|}{P}\diagup OH \\ HO\diagup & (CH_2)_n \diagdown OH \\ & | \\ & S \\ & | \\ & R_2 \end{array}$$

| Code No. | n | R$_2$ | Hydrolysis Conc. of HCl and duration | Product isolated |
|---|---|---|---|---|
| SR 42249 | 0 | (phenyl with CF$_3$) | HCl 12N 10 hrs | Free acid M.p.: 202–204° C. |
| SR 41959 | 6 | (phenyl with Cl) | HCl 6N 12 hrs | Di-(tertiary butylamine salt M.p.: 220–224° C. |
| SR 42143 | 6 | (phenyl with Cl, Cl) | HCl 12N 12 hrs | Di-(tertiary butylamine) salt M.p.: 224–226° C. |

EXAMPLE 12

Monoammonium hexadecylthiomethylene-diphosphonate (SR 41453)

(I) $R_1=H$; $n=0$; $R_2=-(CH_2)_{15}-CH_3$

The procedure of Example 4 is followed, but using, as the solvent, a 40:2 (volume/volume) mixture of toluene and dimethylformamide.

After the mixture has been heated at 100° C. for 20 hours, the corresponding ester is obtained, and this is hydrolyzed by heating under reflux with 12N HCl for 15 hours. The crude acid dissolved in ammonia gives a monoammonium salt; melting point: 103°–110° C.

Following the same procedure but varying the disulfide used, decylthiomethylene-diphosphonic acid is obtained and is isolated in the form of the di-(tertiary butylamine) salt (SR 41457). Melting point: 170°–175° C.

EXAMPLE 13

Di-(tertiary butylamine) salt of (2-hydroxyethylthio)-methylene-diphosphonic acid (SR 41318)

(I) $R_1=H$; $n=0$; $R_2=HO-CH_2CH_2-$ (a) A mixture of 35 g of di-(2-hydroxyethyl)-disulfide, 80 ml of 3,4-dihydro-2H-pyran and 0.1 g of para-toluenesulfonic acid is heated at 70° C. for 1 minute.

The mixture is cooled to 40° C. and stirred for 10 minutes, poured into 200 ml of water and extracted with ether. The ether solution is dried and the solvent is evaporated to dryness, giving 71 g of the disulfide in which the 2 alcohol groups are blocked in the form of the 3,4-dihydro-2H-pyranyl ether.

(b) The above disulfide is condensed with tetraisopropyl methylene-diphosphonate in accordance with the technique of Example 5, the mixture being kept at 20° C. for 3 hours.

(c) The product obtained in the preceding paragraph (18 g) is dissolved in 150 ml of methanol and 2 ml of concentrated hydrochloric acid are added. This mixture is heated under reflux for 1 hour, then concentrated by evaporation of methanol, and poured into 200 ml of water. It is extracted twice with methylene chloride and the extract solution is dried and concentrated to dryness. 13 g of the ester with the protective groups removed are thus obtained.

(d) The ester is hydrolyzed as indicated in Example 4, by heating under reflux with 6N hydrochloric acid for 16 hours.

The acid thus obtained, when treated with tertiary butylamine in ethanol, gives the di-(tertiary butylamine) salt SR 41318; melting point: 168° C.

EXAMPLE 14

Disodium methylthiomethylene-diphosphonate (SR 41553)

(I) $R_1=H$; $n=0$; $R_2=CH_3$ 5 g of methylthiomethylene-diphosphonic acid (Example 4) are dissolved in 50 ml of distilled water containing 1.8 g of dissolved sodium hydroxide.

The solution is filtered, 200 ml of methanol are then added and the mixture is left to crystallize. The precipitate is filtered off and washed with methanol. It is dried at 80° C. in vacuo and the disodium salt (crystallized with ½ molecule of water) is thus obtained; melting point: >270° C.

EXAMPLE 15

Tri-(tertiary butylamine) salt of benzothiazol-2-yl-thiomethylene-diphosphonic acid (SR 41481)

$R_1 = H$; $n = 0$; $R_2 =$ 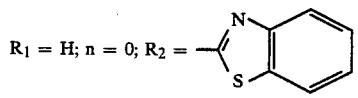 (I)

(a) Di-(benzothiazol-2-yl)-disulfide

A solution of 20 g of iodine and 115 g of potassium iodide in 400 ml of water is added dropwise to a solution of 30 g of 2-mercapto-benzothiazole and 1.6 g of sodium hydroxide in 800 ml of absolute ethanol. After completion of the addition, the mixture is stirred for 30 minutes at ambient temperature and the precipitate is then filtered off, washed with ethanol and then washed with ether.

After drying, 28 g of disulfide are obtained; melting point: 174° C.

(b) The above disulfide is condensed with tetramethyl methylene-diphosphonate using the technique of Example 5 (heating for 2 hours at 20° C.).

(c) 7 ml of trimethylsilyl bromide are added to a solution of 6.5 g of the tetramethyl ester obtained above in 80 ml of carbon tetrachloride at a temperature of 10° C. under a nitrogen atmosphere, and the mixture is stirred for 30 minutes at this temperature.

10 ml of water are added and the aqueous phase is separated off and washed with ether. Evaporation of the aqueous phase gives 4 g of the expected acid. The latter is converted to the tri-(tertiary butylamine) salt by treatment with tertiary butylamine in ethanol; melting point: 202°–204° C.

Following the same method but using di-(thien-2-yl)-disulfide, thien-2-yl-thiomethylene-diphosphonic acid is ultimately obtained, and is isolated in the form of the tri(tertiary butylamine) salt, which crystallizes with 2 molecules of water (SR 41549); melting point 210° C.

EXAMPLE 16

Tertiary-butylammonium 4-(methylthio)-butylidene-1,1-diphosphonate (SR 41177)
(I) $R_1=H$; $n=3$; $R_2=CH_3$ (a) Tetraisopropyl buten-3-ylidene-1,1-diphosphonate 0.5 g of sodium hydride is added in the course of 5 minutes to a mixture of 6.8 g of tetraisopropyl methylenediphosphonate and 20 ml of toluene at 10° C. The mixture is stirred at 15° C. for 1 hour, 15.5 ml of allyl bromide are then introduced and the whole is stirred at 20° C. for 20 hours.

The reaction mixture is taken up in 100 ml of isopropyl ether and 50 ml of water. The organic phase is decanted, washed 3 times with 50 ml of water and then dried and evaporated to dryness. An oil (4.5 g) is obtained, and is distilled in vacuo; boiling point/0.02 mm: 108°-110° C.

(b) Tetraisopropyl 4-(methylthio)-butylidene-1,1-diphosphonate

A mixture of 4.5 g of the product obtained above, 50 ml of methylmercaptan and 0.1 g of benzoyl peroxide is heated at 130° C. in an autoclave for 20 hours.

After the end of the reaction, the reaction mixture is distilled in a very high vacuum and the fraction (3.6 g) which distils at between 120° and 130° C. under $2\times10^{-5}$ mm of mercury is collected.

(c) A mixture of 3.6 g of the ester obtained above and 14 ml of 8N hydrochloric acid is heated under reflux for 14 hours. It is evaporated to dryness in vacuo and the residue is taken up in 30 ml of water and 30 ml of ether.

The aqueous phase is separated off, treated with active charcoal and again evaporated to dryness. The residue is taken up in 20 ml of ethanol and treated with 2.5 ml of tertiary butylamine. Addition of 20 ml of ether gives 1.4 g of the expected salt; melting point: 190° C.

EXAMPLE 17

Di-(tertiary butylamine) salt of 5-mercapto-pentylidene-1,1-diphosphonic acid (SR 41527)

Following the procedure of Example 4, starting from tetraethyl methylene-diphosphonate and 4-acetylthio-1-bromobutane, tetraethyl 5-acetylthio-pentylidene-1,1-diphosphonate is prepared in the form of an oil.

The ester thus obtained is treated with 12N HCl for 7 hours as indicated in Example 9. This hydrolyzes the ester groups and the acetyl group of the thiol, and gives the compound SR 41527, which is isolated in the form of its di-(tertiary butylamine) salt; melting point: 160° C.

EXAMPLE 18

Di-(tertiary butylamine) salt of 7-(1-methyl-imidazol-2-yl-thio)-heptylidene-1,1-diphosphonic acid (SR 42132)

(a) Tetraisopropyl 7-bromo-heptylidene-1,1-diphosphonate is prepared by the method indicated in Example 16(a), using 1,6-dibromohexane.

(b) A solution of 10 g of the above bromine derivative, 2 g of 2-mercapto-1-methyl-imidazole and 0.8 g of sodium hydroxide in 50 ml of 96° ethanol is heated at 80° C. for 2 hours.

The mixture is evaporated to dryness, the residue is taken up in water and the solution is extracted with ether. The ether solution is washed with a 3N sodium hydroxide solution and then with water, dried over sodium sulfate and evaporated to dryness.

The product is chromatographed on a silica column, elution being carried out with a 98:2 (volume/volume) mixture of methylene chloride/methanol. 4 g of the expected ester are thus obtained.

(c) The ester is hydrolyzed with 12N hydrochloric acid by heating under reflux for 16 hours. The expected compound is isolated in the form of the di-(tertiary butylamine) salt; melting point: 158°-162° C.

EXAMPLE 19

Tetraethyl 5-(4-fluoro-phenylthio)-1-hydroxy-pentylidene-1,1-diphosphonate (SR 41906)

8.8 g of triethyl phosphite are added, with stirring, to 12.1 g of 5-(4-fluoro-phenylthio)-valeryl chloride at 30° C., under a nitrogen atmosphere. The reaction mixture is stirred for 3 hours at 35° C. and is then cooled to 0° C., and a mixture of 0.45 ml of dibutylamine and 6.5 ml of diethyl phosphite is introduced in the course of 10 minutes. Stirring is continued at 5° C. for 1 hour and 20 ml of a 1N hydrochloric acid solution and 100 ml of ethyl ether are then added. After having stirred the mixture, the ether layer is separated off and the aqueous phase is re-extracted with 100 ml of methylene chloride. The organic extracts are combined and dried over sodium sulfate, and the solvents are evaporated in vacuo.

The residue is chromatographed on a silica column, elution being carried out with a 95:5 (volume/volume) mixture of methylene chloride/ethanol.

The expected product is thus obtained in the form of a colorless oil (8.7 g).

Chromatography on a thin layer of silica shows an Rf of 0.40 (using a 95:5 (volume/volume) mixture of ethyl acetate/ethanol).

The products (I) listed in the table below are prepared in the same manner, but varying the acid chloride used and/or the phosphite.

TABLE 5

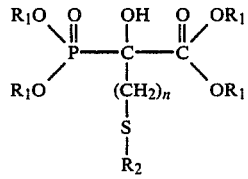

| Code No. | $R_1$ | $R_2$ | n | Characteristics Thin lay chromatography on silica |
|---|---|---|---|---|
| SR 41962 | —$CH_3$ | —$(CH_2)_4$—$CH_3$ | 3 | Colorless oil Rf = 0.40 (80:20 (vol/vol) ethyl acetate/ethanol) |

TABLE 5-continued $$\begin{array}{c} R_1O \diagdown \underset{\|}{O} \quad OH \quad O \diagup OR_1 \\ P-C-C \\ R_1O \diagup \quad (CH_2)_n \quad OR_1 \\ | \\ S \\ | \\ R_2 \end{array}$$

| Code No. | $R_1$ | $R_2$ | n | Characteristics<br>Thin lay chromatography on silica |
|---|---|---|---|---|
| SR 41963 | —$C_2H_5$ | 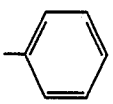 | 2 | Colorless oil<br>Rf = 0.3 (95:5 (vol/vol) ethyl acetate/ethanol) |
| SR 42292 | —$C_2H_5$ | $\begin{array}{c} CH_3 \\ | \\ -C-CH_3 \\ | \\ CH_3 \end{array}$ | 1 | Colorless oil<br>Rf = 0.3 (95:5 (vol/vol) ethyl acetate/ethanol) |
| SR 41940 | —$C_2H_5$ |  | 4 | Colorless oil<br>Rf = 0.5 (90:10 (vol/vol) ethyl acetate/ethanol) |
| SR 41876 | —$C_2H_5$ | 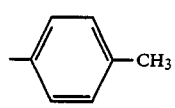 | 3 | Oil<br>Rf = 0.34 (95:5 (vol/vol) ethyl acetate/ethanol) |
| SR 42295 | —$C_2H_5$ | 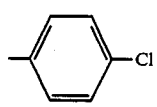 | 4 | Colorless oil<br>Rf = 0.25 (95:5 (vol/vol) ethyl acetate/ethanol) |
| SR 42014 | —$C_2H_5$ | —$(CH_2)_2$—$CH_3$ | 5 | Colorless oil<br>Rf = 0.30 (95:5 (vol/vol) ethyl acetate/ethanol) |
| SR 42089 | —$C_2H_5$ | — $CH_3$ | 10 | Colorless oil<br>Rf = 0.25 (95:5 (vol/vol) ethyl acetate/ethanol) |

EXAMPLE 20

Tetraethyl 5-(pyrid-2-yl-thio)-1-hydroxy-pentylidene-1,1-diphosphonate (SR 42090)

(a) Tetraethyl 5-bromo-1-hydroxy-pentylidene-diphosphonate is prepared in accordance with the technique of Example 19, using 5-bromovaleryl chloride as the acid chloride.

This product is isolated in the form of an oil. Chromatography on a thin layer of silica shows an Rf of 0.4 (using an 80:20 (volume/volume) mixture of ethyl acetate/ethanol).

(b) A mixture of 2.2 g of 2-mercapto-pyridine and 2 g of 1,5-diaza-bicyclo(5.4.0)-undec-5-ene in 6 ml of acetonitrile is added in the course of 15 minutes to a solution of 4.4 g of the preceding product in 5 ml of acetonitrile, cooled to 0° C. The mixture is stirred for 1 hour at 0° C. and then chromatographed on a silica column (150 g). After washing the column with methylene chloride, elution is carried out with a 95:5 (volume/volume) mixture of methylene chloride/ethanol.

The expected product is obtained in the form of a yellowish oil. Thin layer chromatography on silica shows an Rf of 0.15 (using a 95:5 (volume/volume) mixture of ethyl acetate/ethanol).

Following the same procedure but replacing the 5-bromovaleryl chloride in (a) by 6-bromohexanoyl chloride, diethyl 6-bromo-1-hydroxy-hexylidene-1,1-diphosphonate is obtained.

This compound, when treated by the method indicated in paragraph (b) with 5-chloro-2-mercapto-benzothiazole, gives tetraethyl 6-[(5-chloro-benzothiazol-2-yl)-thio]-1-hydroxyhexylidene-1,1-diphosphonate (SR 42294) in the form of a colorless solid. Melting point: 72° C. (after crystallization from isopropyl ether).

EXAMPLE 21

Di-(tertiary butylamine) salt of 4-(4-chlorophenylthio)-1-hydroxy-butylidene-1,1-diphosphonic acid (SR 41903)

A mixture of 5 g of tetraethyl 4-(4-chlorophenylthio)-1-hydroxy-butylidene-1,1-diphosphonate and 50 ml of 12N hydrochloric acid is refluxed for 12 hours under nitrogen. The mixture is evaporated to dryness in vacuo, the residue is then dissolved in 100 ml of distilled water and the solution is washed twice with 100 ml of ether. The aqueous phase is evaporated to dryness. A colorless solid remains, which is dissolved in 30 ml of isopropanol and treated with 3.6 ml of tertiary butylamine. The precipitate is filtered off and washed with isopropanol, acetone and finally ether. After having dried the product in vacuo, a colorless solid (4 g) is obtained; melting point: 202°–205° C. (decomposition).

Following the same procedure but starting from the ester SR 42090 (Example 20), 5-(pyrid-2-yl-thio)-pentylidene-1,1-diphosphonic acid is obtained; it is isolated in the form of the free acid (SR 42099); melting point: 194°–7° C. (after crystallization from isopropanol).

The sirupy residue is converted to the dibutylamine salt by the method indicated in Example 21. Finally, a colorless solid is obtained; melting point: 211°–5° C.

Following the same procedure but starting from various esters obtained previously, the acids shown in the table which follows are obtained.

TABLE 6

$$\begin{array}{c} HO\diagdown\underset{\|}{P}\!-\!\underset{|}{\overset{OH}{\underset{|}{C}}}\!-\!\underset{\|}{P}\diagup OH \\ HO\diagup\quad \underset{|}{(CH_2)_n}\quad \diagdown OH \\ \quad S \\ \quad | \\ \quad R_2 \end{array}$$

| Code No | n | R$_2$ | Form in which isolated / Characteristics |
|---|---|---|---|
| SR 42142 | 10 | –C$_6$H$_4$–CH$_3$ (para) | Di-(tertiary butylamine) salt<br>M.p.: 242–246° C. |
| SR 42097 | 10 | –CH$_3$ | Di-(tertiary butylamine) salt<br>M.p.: 195–200° C. (decomposition) |
| SR 42304 | 5 | 2-(4-chlorophenyl)thiazol-5-yl | Free acid. Crystallizes with 1 molecule of water.<br>M.p.: 205–208° C. |
| SR 42015 | 5 | –CH$_2$CH$_2$CH$_3$ | Salt with 2.5 molecules of tertiary butylamine<br>M.p.: 202–205° C. (decomposition) |
| SR 42296 | 4 | 2-(4-chlorophenyl)thiazol-5-yl | Free acid<br>M.p.: 165–168° C. |
| SR 42016 | 4 | –C$_6$H$_4$–CH$_3$ (para) | Disodium salt<br>M.p.: >300° C. |
| SR 42293 | 1 | –C(CH$_3$)$_3$ | Tertiary butylamine salt (1.75 moles)<br>M.p.: 220–225° C. (decomposition) |
| SR 41961 | 3 | –(CH$_2$)$_4$–CH$_3$ | Tertiary butylamine salt (1.5 moles)<br>M.p.: 175–178° C. |
| SR 42017 | 2 | –C$_6$H$_5$ | Free acid<br>M.p. 145–148° C. |

EXAMPLE 22

Di-(tertiary butylamine) salt of 5-(4-fluorophenylthio)-1-hydroxy-pentylidene-1,1-diphosphonic acid (SR 41909)

5 ml of trimethylbromosilane are added to a stirred solution, cooled to 10° C., of the ester SR 41906 (Example 19) in 15 ml of carbon tetrachloride and the mixture is left for 40 hours at 25° C. 40 ml of water are added and the mixture is stirred for 1 hour. The aqueous phase is decanted, washed twice with 30 ml of methylene chloride and evaporated to dryness in vacuo. The residue is taken up in 30 ml of water and this solution is again evaporated to dryness in vacuo.

The compounds according to the invention are advantageously used as anti-inflammatory and anti-rheumatic drugs and their pharmacological properties have been demonstrated as follows.

IN VITRO STUDY

The in vitro study is based on the fact that chondrocytes in a culture secrete neutral proteinases after stimulation by a factor synthesized by peritoneal macrophages or by the mononuclear cells of the blood.

The involvement of this type of stimulation in rheumatic conditions has been clearly demonstrated in numerous publications.

The principle of the test hence consists in studying the secretion of neutral proteinases by stimulated chondrocytes treated with the products in comparison with the secretion of the stimulated but untreated chondrocytes.

The following procedure was used.

Preparation of the chondrocytes

The chondrocytes are isolated from cartilage from the nasal septum of the calf or from articular cartilage of the rabbit, by enzymatic digestion, and are cultured in DMEM medium containing 10% of calf serum, to a density of $5 \times 10^{15}$ cells per 10 cm Petri dish. The culture medium is renewed every 48 hours.

After one week's culture, the cells are sub-cultured by treatment with trypsin EDTA. The cells are then again cultured in DMEM medium containing 10% of fetal calf serum to a density of $2 \times 10^5$ cells per 16 mm dish. Confluence occurs after 3 days' culture.

Preparation of the conditioned medium of peritoneal macrophages

The peritoneal macrophages of the rabbit are obtained by the method described by DESHMUKH-PHADKE et al., Biochemical Biophysical Research Communication, 85, 490-6, (1978).

The mononuclear cells of human blood are prepared and cultured in accordance with the procedure of DAYER et al. [The Journal of Immunology, 124, 1712-1720 (1980)].

After culture, the medium containing the "chondrocyte stimulating factor" is recovered, filtered on an $0.22\mu$ Millipore filter and frozen at $-2G°$ C.

Stimulation of the chondrocytes

At the time of confluence, the culture medium of the chondrocytes is replaced by DMEM medium containing 1% of fetal calf serum, mixed with 20% of medium containing the chondrocyte stimulating factor.

The products to be tested are introduced into the culture medium at the same time as the stimulation medium, at a concentration which avoids cytotoxicity of the product or insolubility of the product. After 3 days' culture, the medium is recovered in order to determine its content of neutral proteinases.

Determination of the neutral proteinases

The procedure of VAES et al. Biochemical Journal, 172, 261, (1978) is used.

The results obtained with the various products of the invention are listed in Table 7. They are expressed as a percentage inhibition of the secretion of neutral proteinases by stimulated chondrocytes treated with the products to be studied, relative to that of stimulated chondrocytes not treated with the products.

TABLE 7

| Code No. of the product | Chondrocyte in culture % inhibition | Code No. of the product | Chondrocyte in culture % inhibition |
|---|---|---|---|
| SR 41 036 | 72 ± 8 | SR 41 319 | 85 ± 1 |
| SR 41 100 | 20 ± 1 | SR 41 179 | 75 ± 7 |
| SR 41 421 | 97 ± 2 | SR 41 264 | 50 ± 10 |
| SR 41 457 | 95 ± 3 | SR 41 263 | 90 ± 1 |
| SR 41 453 | 40 ± 2 | SR 41 480 | 56 ± 9 |
| SR 41 266 | 68 ± 8 | SR 41 481 | 74 ± 9 |
| SR 41 344 | 31 ± 6 | SR 41 177 | 69 ± 4 |
| SR 41 482 | 83 ± 6 | SR 41 342 | 99 ± 1 |
| SR 41 456 | 98 ± 1 | SR 41 388 | 90 ± 1 |
| SR 41 908 | 82 ± 2 | SR 41 960 | 55 ± 4 |
| SR 41 689 | 90 ± 3 | SR 41 690 | 97 ± 1 |
| SR 41 688 | 94 ± 1 | SR 42 249 | 92 ± 4 |

TABLE 7-continued

| Code No. of the product | Chondrocyte in culture % inhibition | Code No. of the product | Chondrocyte in culture % inhibition |
|---|---|---|---|
| SR 41 549 | 58 ± 4 | SR 41 687 | 89 ± 2 |
| SR 41 527 | 54 ± 3 | SR 41 959 | 79 ± 2 |
| SR 41 625 | 92 ± 0 | SR 42 099 | 50 ± 5 |

IN VIVO STUDY: Adjuvant arthritis

The injection of Mycobacterium into the rat causes a polyarthritis which in certain respects resembles human rheumatoid arthritis.

Procedure

A suspension of Mycobacterium tuberculosis (0.4 mg per 0.05 ml of medicinal paraffin) is injected intradermally into the tail of male Sprague-Dawley rats having an average weight of 150 g.

After 15 days, the animals exhibiting the most marked arthritis symptoms are selected. These rats are divided into groups of 5 animals, and each group is then treated cutaneously with the product to be studied at a dose of 10 mg/kg per day for 6 days per week. One of the groups is only given solvent and serves as the reference group.

After 3 weeks' treatment, the animals are sacrificed and the right rear paw is removed at the tibiotarsal joint and then weighed.

For each group, the mean and the standard error of these weights is determined.

The activity of each product is expressed in terms of the difference in percent of the average weight of the paws of the treated arthritic rats relative to that of the arthritic paws of the reference rats.

The results obtained with various products of the invention are listed in Table 8.

TABLE 8

| Code No. of the product | Adjuvant arthritis Weight of the paw % inhibition | Code No. of the product | Adjuvant arthritis Weight of the paw % inhibition |
|---|---|---|---|
| SR 41 036 | 23 | SR 41 319 | 29 |
| SR 41 100 | 37 | SR 41 452 | 15 |
| SR 41 421 | 55 | SR 41 272 | 25 |
| SR 41 454 | 33 | SR 41 179 | 25 |
| SR 41 453 | 58 | SR 41 264 | 43 |
| SR 41 266 | 29 | SR 41 263 | 19 |
| SR 41 344 | 35 | SR 41 273 | 39 |
| SR 41 388 | 42 | SR 41 552 | 36 |
| SR 41 482 | 41 | SR 41 689 | 31 |
| SR 41 690 | 35 | SR 41 319 | 35 |
| SR 41 688 | 38 | SR 41 549 | 34 |
| SR 41 480 | 40 | SR 41 481 | 40 |
| SR 41 342 | 38 | SR 41 687 | 38 |
| SR 41 527 | 34 | SR 41 959 | 60 |
| SR 41 341 | 24 | SR 42 017 | 49 |
| SR 41 961 | 53 | SR 41 903 | 55 |
| SR 41 903 | 55 | SR 42 016 | 48 |
| SR 41 909 | 53 | SR 42 099 | 44 |
| SR 42 015 | 47 | SR 42 097 | 50 |

Moreover, the products according to the invention are of low toxicity.

They can be used in human therapy for the treatment of conditions due to inflammatory phenomena and in particular for the treatment of arthritic conditions. In particular, the compounds according to the invention can be used in the treatment of rheumatoid polyarthritis.

The compounds according to the invention can be presented in forms suitable for oral, endorectal and parenteral administration.

These forms can in particular be pills or tablets containing an amount of active principle from 10 to 500 mg per unit.

The daily posology of these products in an adult can be of the order of 100 mg to 5 g, taken in several portions.

The following galenical composition may be given by way of example:

| PILLS | |
| --- | --- |
| CM 41 421 | 200 mg |
| Aerosil | 1 mg |
| Magnesium stearate | 3 mg |
| Starch STA RX 1500 | 96 mg |
| | 300 mg |

We claim:

1. A method for treating inflamation which comprises administering to an animal in need of such treatment an anti-inflammatory effective amount of a methylenediphosphonic acid compound having the formula

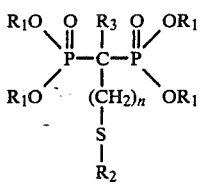

in which:

$R_1$ is hydrogen or a straight or branched lower alkyl group having from 1 to 4 carbon atoms, $R_2$ is:
hydrogen,
an alkyl group having from 1 to 16 carbon atoms which is unsubstituted or substituted by a phenyl group, a hydroxyl group, a thiol group, one or more halogen atoms,

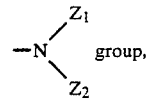

where $Z_1$ and $Z_2$, considered independently of one another, are hydrogen or a lower alkyl group,
a phenyl group which is unsubstituted or substituted one or more times by halogen, a nitro group, a lower alkyl group, a lower alkoxy group, trifluoromethyl, an $NH_2$ group, or a COOH group, or

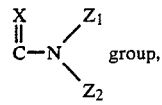

where X is oxygen or sulfur and $Z_1$ and $Z_2$ are as defined above,
$R_3$ is hydrogen or a hydroxyl group, and
n is an integer between 0 and 10, except that n cannot be 0 if $R_3$ is OH, or a salt of such compound with an organic or inorganic bases when $R_1 = H$.

2. The method of claim 1 wherein the anti-inflammatory effective amount contains from 10 to 500 mg and is administered orally, endorectally, or parenterally.

* * * * *